United States Patent [19]
Satzinger et al.

[11] Patent Number: 4,760,081
[45] Date of Patent: * Jul. 26, 1988

[54] 1,6-NAPHTHYRIDINE DERIVATIVES USEFUL FOR TREATING DISEASES OF THE BLOOD VESSELS

[75] Inventors: Gerhard Satzinger, Denzlingen; Johannes Hartenstein, Stegen-Wittental; Karl Mannhardt, Elzach-Oberprechtal; Jürgen Kleinschroth, Denzlingen; Hartmut Osswald, Waldkirch; Günter Weinheimer, Denzlingen; Edgar Fritschi, St. Peter, all of Fed. Rep. of Germany

[73] Assignee: Goedecke Aktiengesellschaft, Berlin, Fed. Rep. of Germany

[ * ] Notice: The portion of the term of this patent subsequent to Dec. 8, 2004 has been disclaimed.

[21] Appl. No.: 7,686

[22] Filed: Jan. 28, 1987

Related U.S. Application Data

[63] Continuation-in-part of Ser. No. 891,712, Jul. 30, 1986, Pat. No. 4,711,901, which is a continuation-in-part of Ser. No. 767,989, Aug. 21, 1985, abandoned.

[30] Foreign Application Priority Data

Aug. 25, 1984 [DE] Fed. Rep. of Germany ....... 3431303
Jan. 29, 1985 [DE] Fed. Rep. of Germany ....... 3502790
Jan. 29, 1986 [DE] Fed. Rep. of Germany ....... 3602655

[51] Int. Cl.$^4$ .................. A61K 31/435; C07D 471/04
[52] U.S. Cl. .................... 514/300; 540/597; 546/123
[58] Field of Search .............. 546/123; 540/597; 514/212, 300

[56] References Cited
PUBLICATIONS
Schramm et al., Nature, vol. 303, pp. 535–537 (1983).

Primary Examiner—Mary C. Lee
Assistant Examiner—Bernard I. Dentz
Attorney, Agent, or Firm—Elizabeth M. Anderson

[57] ABSTRACT

The present invention describes 1,6-naphthyridine derivatives of the general formula:

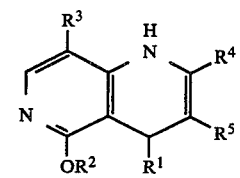

wherein $R^1$ is an unsubstituted or substituted aromatic or heteroaromatic ring, $R^2$ is a straight-chained or branched alkyl radical containing up to four carbon atoms or a benzyl radical, $R^3$ is a hydrogen atom, a straight-chained or branched alkyl radicals or an alkoxycarbonyl radical containing up to four carbon atoms, $R^4$ is a straight-chained or branched alkyl radical containing up to four carbons and $R^5$ is a carboxyl group or a straight-chained, branched or cyclic alkoxycarbonyl radical which contains up to 17 carbon atoms and optionally also contains an oxygen, sulphur or nitrogen atom; as well as the pharmacologically acceptable salts thereof, which are useful for treating diseases of the blood vessels.

3 Claims, No Drawings

1,6-NAPHTHYRIDINE DERIVATIVES USEFUL FOR TREATING DISEASES OF THE BLOOD VESSELS

This is a continuation-in-part of U.S. Ser. No. 891,712 filed July 30, 1986 now U.S. Pat. No. 4,711,901 which is a continuation-in-part of U.S. Ser. No. 767,989 filed Aug. 21, 1985, now abandoned.

SUMMARY OF THE INVENTION

The present invention is concerned with new 1,6-naphthyridine derivatives, with the preparation thereof and with pharmaceutical compositions containing them.

The new 1,6-naphthyridine derivatives according to the present invention are compounds of the general formula:

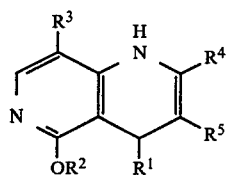
(I)

wherein $R^1$ is an unsubstituted or substituted aromatic or heteroaromatic ring, $R^2$ is a straight-chained or branched alkyl radical containing up to four carbon atoms or a benzyl radical, $R^3$ is hydrogen atom, a straight-chained or branched alkyl radical or an alkoxycarbonyl radical containing up to five carbon atoms, $R^4$ is a straight-chained or branched alkyl radical containing up to four carbons and $R^5$ is a carboxyl group or a straight-chained, branched or cyclic alkoxycarbonyl radical which contains up to 17 carbon atoms and which chain may be interrupted by oxygen, sulphur or nitrogen atom; as well as the pharmacologically acceptable salts thereof.

DETAILED DESCRIPTION OF PREFERRED EMBODIMENTS

As aromatic or heteroaromatic rings $R^1$, there are preferred phenyl, thienyl, pyridyl, or 2,1,3-benzoxadiazolyl radicals which are unsubstituted or substituted once or twice by lower polar or non-polar radicals.

1,6-Naphthyridine derivatives of general formula (I) are preferred in which $R^1$ is a phenyl radical mono- or disubstituted by halogen, cyano, nitro, lower alkyl, lower alkoxy, difluoromethoxy, trifluoromethoxy, lower alkylenedioxy, such as methylenedioxy, lower alkylamino, especially dimethyl- or diethylamino, methylthio, difluoromethylthio, or trifluoromethyl radicals, or is a thienyl, pyridyl or 2,1,3-benzoxadiazolyl radical, $R^3$ is preferably a hydrogen atom, an alkyl radical containing up to four carbon atoms or an alkoxycarbonyl radical containing up to five carbon atoms, $R^4$ is preferably an alkyl radical containing up to three carbon atoms and especially a methyl or ethyl radical and $R^5$ is preferably a carboxyl group or an alkoxycarbonyl radical containing up to 17 carbon atoms. Complex or voluminous radicals can here be present which possibly contain further heteroatoms, such as oxygen, sulphur or nitrogen atoms. Typical examples of such radicals include amines, such as lower N-benzyl-N-alkylaminoalkyl radicals, N,N-dialkylaminoalkyl radicals or lower alkylthioalkyl of alkoxyalkyl radicals.

Unless otherwise specified, lower "alk" refers to a carbon chain, straight or branched, having up to six carbon atoms.

Especially preferred at 1,6-naphthyridine derivatives of general formula (I) in which $R^1$ is a phenyl radical optionally substituted preferably in the 2- or 3-position by halogen, cyano, nitro, methyl, methoxy, difluoromethoxy or trifluoromethyl or is a phenyl radical preferably substituted in the 2,3- or 2,6-position by halogen atoms, which can be the same or different, or is an unsubstituted thienyl radical, $R^2$ is a methyl, ethyl, n-propyl, isopropyl, n-butyl, sec-butyl, isobutyl or benzyl radical, $R^3$ is a hydrogen atom, preferably a methyl but also an ethyl or isopropyl radical or an alkoxycarbonyl radical of the general formula:

$$-CO_2R^6 \quad (II)$$

in which $R^6$ is a methyl, ethyl, propyl or isopropyl radical and especially an ethyl radical, $R^4$ is a methyl or ethyl radical and $R^5$ is a carboxy group or an alkoxycarbonyl radical of the general formula:

$$-CO_2R^7 \quad (III)$$

in which $R^7$ is a hydrogen atom, a methyl, ethyl, propyl, isopropyl, n-butyl, isobutyl, tert-butyl or benzyl radical, an alkoxyalkyl or alkylthioalkyl radical of the general formula:

$$-(CH_2)_n-O-R^8 \quad (IV)$$

or

$$-(CH_2)_n-S-R^8 \quad (V)$$

in which $R^8$ is an alkyl radical containing up to three carbon atoms and n is two or three, or an aminoalkyl radical of the general formula:

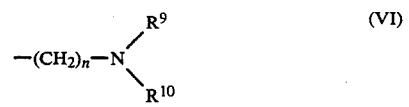
(VI)

in which $R^9$ and $R^{10}$ can be the same or different and are hydrogen atoms, straight-chained or branched alkyl radicals containing up to four carbon atoms or benzyl radicals or together form a lower alkylene radical containing four to six carbon atoms and n is two or three.

The present invention also provides a process for the preparation of 1,6-naphthyridine derivatives of general formula (I), wherein 1,6-naphthyridinone derivatives of the general formula:

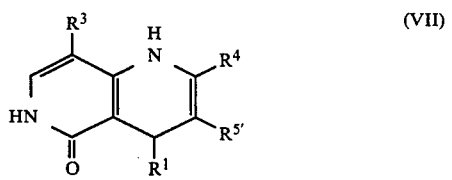
(VII)

in which $R^1$, $R^3$, and $R^4$ have the same meanings as above and $R^{5'}$ is an alkoxycarbonyl radical of general formula (III), are alkylated in known manner.

Compounds of general formula (I), in which $R^5$ is a carboxyl group, are preferably prepared from compounds of general formula (I), in which $R^5$ is a benzyloxycarbonyl radical, by hydrogenolytic fission in known manner.

The compounds of general formula (VII) can be prepared, for example, in the manner described in Federal Republic of Germany Patent Application Number P 33 27 650, in that either (a) a dihydropyridine of the general formula:

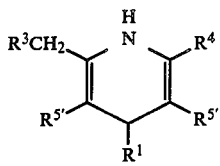

in which $R^1$, $R^3$, $R^4$, and $R^{5'}$ have the same meanings as above, is reacted with s-triazine in the presence of a base, (b) a 1,4-dihydropyridine of general formula (VIII) is reacted with a dialkylformamide dialkyl acetal of the general formula:

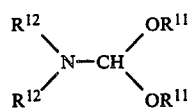

in which the $R^{12}$ substituents can be the same or different and are methyl or ethyl radicals and each of the $R^{11}$ substituents is an alkyl radical containing up to four carbons or the two $R^{11}$ substituents together represent an alkylene radical containing up to three carbon atoms, and the compound obtained of the general formula:

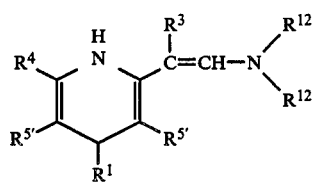

in which $R^1$, $R^3$, $R^4$, $R^{5'}$, and $R^{12}$ have the same meanings as above, is reacted with ammonia, or (c) 2,4-dihydroxypyridine is reacted with a compound of the general formula:

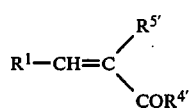

in which $R^1$ and $R^{5'}$ have the same meanings as above and $R^{4'}$ is a straight-chained or branched alkyl radical containing up to four carbon atoms, in the presence of ammonia.

The compounds of general formula (XI) are known or can be prepared by processes known from the literature (see. Org. Reactions, 15, 204 et seq., 1967). 2,4-Dihydroxypyridine is commercially available.

The 1,4-dihydropyridines of general formula (VIII) used for processes (a) and (b) are known (cf., for example, Chem. Rev., 82, 223, 1982) or can be prepaed in an analogous manner.

For carrying out process (a), the 1,4-dihydropyridine derivative is heated with s-triazine in an inert organic solvent in the presence of a strong base, for example an alkali metal alcoholate or sodium hydride, to a temperature of from 50° to 160° C. and preferably of from 100° to 150° C. As solvents, there are here especially preferred polar solvents, such as dimethyl sulphoxide, dimethylformamide, ethylene glycol dimethyl ether or lower alcohols, such as ethanol.

For carrying out the reaction according to process variant (b), the appropriate 1,4-dihydropyridine derivative is reacted with an equivalent or excess amount of dialkyl formamide dialkyl acetal, preferably in the presence of an aprotic solvent, such as dimethylformamide, dimethyl sulphoxide or hexamethylphosphoric acid triamide, while heating. Especially preferred formamide acetals include dimethylformamide dimethyl acetal and dimethylformamide diethyl acetal.

The intermediate of general formula (X) obtained according to process variant (b) is converted into a compound of general formula (VII) by reaction with ammonia in the presence of a preferably aprotic solvent at ambient temperature or at an elevated temperature, preferably at the boiling point of the solvent used. As solvents, there are especially preferred lower alcohols, such as methanol or ethanol.

Reaction (c) is preferably carried out in inert organic solvents, especially lower alcohols, such as methanol, ethanol or isopropanol. It is also expedient to work at elevated temperatures, preferably at the boiling temperature of the solvent used. The reaction products can be isolated and purified by known separation processes, such as crystallization and/or chromatography.

The preparation of the 1,6-naphthyridine derivatives of general formula (I) takes place, according to the present invention, according to conventional processes described in the literature for the O-alkylation of lactams (cf. Adv. Heterocyclic Chem., 12, 185–212, 1970). Appropriate alkylation agents include alkyl halides and alkyl sulphonates, dialkyl sulphates and trialkyloxonium salts.

For the reaction with alkyl halides, the compounds of general formula (VII) are used in the form of their metal salts, preferably of their alkali metal or silver salts, which are either prepared separately or are produced in situ with the help of appropriate bases, such as metal hydrides, carbonates or alkoxides in aprotic solvents.

As appropriate solvents, depending upon the alkylation agent used, there can be used practically all inert organic solvents, such as open-chained, cyclic or also aromatic hydrocarbons, for example n-pentane, n-hexane, cyclohexane, benzene or toluene, halogenated hydrocarbons, such as dichloromethane or 1,2-dichloroethane, ethers, such as diethyl ether or 1,2-dimethoxyethane, as well as dipolar aprotic solvents, such as dimethylformamide, hexamethylphosphoric acid triamide and dimethyl sulphoxide. Depending upon the solvent used, the temperature range can be varied between −20° C. and the boiling point of the solvent in question.

Because of the ambident character of the lactam anion, in the case of the alkylation there are frequently obtained mixtures of O- and N-alkylation products, depending upon the reaction conditions and the alkylation agent used (see. J. Org. Chem., 32, 4040 et seq., 1967). The product mixtures obtained may be separated by chromatographic methods and/or by crystallization.

The 1,6-naphthyridine derivatives of general formua (I) in which $R^2$ is a methyl or ethyl radical are preferably obtained by reaction of the 1,6-naphthyridinones of general formula (VII) with trimethyl or triethyloxonium salts, especially trimethyloxonium tetrafluoroborate, in an aprotic solvent. The preparation of the O-propyl, O-isopropyl, O-butyl, O-sec-butyl, O-isobutyl and O-benzyl compounds, on the other hand, is preferably carried out by alkylation of the alkali metal salts with appropriate alkyl- or benzyl halides.

Acidic or basic compounds of general formula (I), in which $R^5$ is a carboxyl group or an unsubstituted or substituted aminoalkoxycarbonyl radical, are, for the purpose of purification and for galenical reasons, preferably converted into crystalline, pharmacologically acceptable salts.

When $R^5$ is a carboxyl group, with the use of bases, for example hydroxides or carbonates, there can be prepared the corresponding salts of the alkali metals or alkaline earth metals. When the substituents $R^4$ and/or $R^5$ have a basic character, salts are obtained in conventional manner by neutralization of the bases with appropriate inorganic or organic acids. As acids, there can be used, for example, hydrochloric acid, sulphuric acid, phosphoric acid, hydrobromic acid, acetic acid, tartaric acid, lactic acid, citric acid, malic acid, salicylic acid, ascorbic acid, malonic acid, or succinic acid.

Since the compounds of general formula (I) according to the present invention have a chiral center on C4, they can be present either as racemic mixtures or in the form of the enantiomers.

The compounds of general formula (I) are highly effective calcium antagonists. In contradistinction to known calcium antagonists, at therapeutic concentrations a cardiodepression (negative inotropic, negative chronotropic action is not to be expected.

On the basis of their blood vessel spasmolytic actions, they are especially indicated in the case of cerebral, cardial, and peripheral blood vessel diseases, such as myocardial ischaemia, cerebral infarct, pulmonary thromboses and arteriosclerosis and other stenotic indications, especially because, in comparison with known compounds with a similar mode of action, negative inotropic side effects are substantially absent. Therefore, the 1,6-naphthyridine derivatives of the present invention are valuable agents for combating heart-circulation mortality.

Consequently, a further subject of the present invention is the use of 1,6-naphthyridine derivatives of general formula (I) for combating blood vessel diseases.

The compounds of general formula (I) according to the present invention can be administered orally or parenterally in liquid or solid form. As injection solution, water is preferably used which contains the additives usual in the case of injection solution, such as stabilizing agents, solubilizing agents or buffers.

Additives of this kind include, for example, tartrate and citrate buffers, ethanol, complex formers (such as ethylenediamine-tetraacetic acid and the nontoxic salts thereof), as well as high molecular weight polymers (such as liquid polyethylene oxide) for viscosity regulation. Solid carrier materials include, for example, starch, lactose, mannitol, methyl cellulose, talc, highly dispersed silicic acids, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, also contain flavoring and/or sweetening agents.

Individual dosages to be administered enterally are in the range of from about 5 to 250 mg and preferably from 20 to 100 mg. Parenterally, about 1 to 20 mg are administered.

The following examples are given for the purpose of illustrating the present invention.

EXAMPLE 1

Methyl (±)-4-(2-fluorophenyl)-1,4-dihydro-5-isopropoxy-2-methyl-1,6-naphthyridine-3-carboxylate 1.1 g (37 mMol) sodium hydride (80% in paraffin oil) are suspended in 70 ml dry dimethylformamide and a solution of 10 g (32 mMol) methyl (±)-4-(2-fluorophenyl)-1,4,5,6-tetrahydro-2-methyl-5-oxo-1,6-naphthyridine-3-carboxylate in 100 ml dimethylformamide is added dropwise thereto at ambient temperature, while stirring. After cessation of the evolution of gas, the reaction mixture is further stirred for 30 minutes at ambient temperature. 5.9 g (35 mMol) isopropyl iodide in 30 ml dimethylformamide are then added. Stirring is continued for 20 minutes at ambient temperature, then solvent is evaporated off in a rotary evaporator and the oily residue is stirred with 100 ml water. The resulting pale brown crystalline mass is filtered off with suction, washed with water and dried.

For purification of the crude product, it is crystallized from a mixture of 400 ml ethyl acetate and 50 ml methanol, the O-alkylation product remaining in highly enriched form in the mother liquor as a readily soluble component. This is first chromatographed over silica gel with dichloromethane/methanol (9:1 v/v), starting material still present thereby being completely separated. Further chromatography over silica gel with toluene/ethyl acetate (3:1 v/v) gives almost pure methyl (±)-4-(2-fluorophenyl)-1,4-dihydro-5-isopropoxy-2-methyl-1,6-naphthyridine-3-carboxylate ($R_f$=0.3). Finally, crystallization from n-hexane/diisopropyl ether gives TLC-pure crystals; m.p. 164°–165° C.

The methyl (±)-4-(2-fluorophenyl)-1,4,5,6-tetrahydro-2-methyl-5-oxo-1,6-naphthyridine-3-carboxylate used as starting material is prepared as follows:

A solution of 31.5 g (120 mMol) dimethyl 4-(2-fluorophenyl)-1,4-dihydro-2,6-dimethylpyridine-3,5-dicarboxylate in 260 ml dimethylformamide is added dropwise, under an atmosphere of nitrogen, to a suspension of 3.8 g (130 mMol) sodium hydride (80% in paraffin oil) in 60 ml dry dimethylformamide. Upon slowing down of the evolution of gas, the reaction mixture is further stirred for ten minutes at ambient temperature and subsequently 10.0 g (120 mMol) s-triazine in 260 ml dimethylformamide are added dropwise thereto. The reaction mixture is heated to 110° C. for 16 hours and, after cooling, evaporated in a vacuum. The dark residue is stirred with 600 ml acetone, filtered and the filtrate evaporated in a vacuum. The crude product is boiled with 300 ml methanol, the crystals formed after cooling are filtered off and, for further purification, are recrystallized from methanol. There is obtained methyl (±)-4-(2-fluorophenyl)-1,4,5,6-tetrahydro-2-methyl-5-oxo-1,6-naphthyridine-3-carboxylate in the form of pale beige crystals; m.p. 315°–316° C. (decomp.).

The following compounds are obtained in an analogous manner:
methyl (±)-4-(2-bromoethyl)-1,4-dihydro-5-isopropoxy-2-methyl-1,6-naphthyridine-3-carboxylate (1.a); mp 201°–202° C., recrystallized from diisopropyl ether methyl (±)-1,4-dihydro-5-isopropoxy-2-methyl-4-(2-nitrophenyl)-1,6-naphthyridine-3-carboxylate (1.b); mp 170° C., recrystallized from diisopropyl ether/methanol methyl (±)-1,4-dihydro-5-isopropoxy-2-methyl-4-phenyl-1,6-naphthyridine-3-carboxylate (1.c); mp 132°–133° C., recrystallized from n-hexane methyl (±)-4-(3-chloro-2-fluorophenyl)-1,4-dihydro-5-isopropoxy-2-methyl-1,6-naphthyridine-3-carboxylate (1.d); mp 166°–167° C., recrystallized from n-hexane methyl (±)-1,4-dihydro-5-isopropoxy-2-methyl-4-(3-nitrophenyl)-1,6-naphthyridine-3-carboxylate (1.e); mp 174°–175° C., recrystallized from n-hexane methyl (±)-1,4-dihydro-5-isopropoxy-2-methyl-4-(2-trifluoromethylphenyl)-1,6-naphthyridine-3-carboxylate (1.f); mp 199°–200° C., recrystallized from diisopropyl ether methyl (±)-4-(2-chloro-6-fluorophenyl)-1,4-dihydro-5-isopropoxy-2-methyl-1,6-naphthyridine-3-carboxylate (1.g); mp 194°–195° C., recrystallized from diisopropyl ether methyl (±)-1,4-dihydro-2-methyl-5-propoxy-4-(2-trifluoromethylphenyl)-1,6-naphthyridine-3-carboxylate (1.h); mp 151°–152° C., recrystallized from n-hexane/diisopropyl ether methyl (±)-4-(2-bromophenyl)-5-ethoxy-1,4-dihydro-2-methyl-1,6-naphthyridine-3-carboxylate (1.i); mp 203°–204° C., recrystallized from toluol/ethyl acetate ethyl (±)-5-butoxy-1,4-dihydro-2-methyl-4-(2-trifluoromethylphenyl)-1,6-naphthyridine-3-carboxylate (1.j); mp 107°–109° C., recrystallized from n-hexane 2-methoxyethyl (±)-1,4-dihydro-5-isopropoxy-2-methyl 4-(3-nitrophenyl)-1,6-naphthyridine-3-carboxylate (1.k); mp 174°–175° C., recrystallized from diisopropyl ether ethyl (±)-1,4-dihydro-5-isopropoxy-2-methyl-4-(2-trifluoromethylphenyl)-1,6-naphthyridine-3-carboxylate (1.l); mp 102°–103° C., recrystallized from n-hexane isopropyl (±)-1,4-dihydro-5-isopropoxy-2-methyl-4-(2-trifluoromethylphenyl)-1,6-naphthyridine-3-carboxylate (1.m); mp 111°–112° C., recrystallized from n-hexane isobutyl (±)-1,4-dihydro-5-isopropoxy-2-methyl-4-(2-trifluoromethylphenyl)-1,6-naphthyridine-3-carboxylate (1.n); mp 115°–116° C., recrystallized from n-hexane ethyl (±)-4-(2,3-dichlorophenyl)-1,4-dihydro-5-isopropoxy-2-methyl-1,6-napthyridine-3-carboxylate (1.o); mp 272°–273° C., recrystallized from diisopropyl ether ethyl (±)-5-sec-butoxy-1,4-dihydro-2-methyl-4-(2-trifluoromethylphenyl)-1,6-napthyridine-3-carboxylate hydrochloride (1.p); mp 148°–150° C., recrystallized from diisopropyl ether/ethyl acetate ethyl (±)-1,4-dihydro-5-isobutoxy-2-methyl-4-(2-trifluoromethylphenyl)-1,6-naphthyridine-3-carboxylate (1.q); mp 118°–119° C., recrystallized from petroleum ether (bp 60°–80° C.)

tert-butyl (±)-1,4-dihydro-5-isopropoxy-2-methyl-4-(2-trifluoromethylphenyl)-1,6-naphthyridine-3-carboxylate (1.r); mp 209° C. recrystallized from n-hexane/diisopropyl ether ethyl (±)-2-ethyl-1,4-dihydro-5-isopropoxy-8-methyl-4-phenyl-1,6-naphthyridine-3-carboxylate (1.s); mp 176°–177° C., recrystallized from n-hexane/diisopropyl ether 2-(N-benzyl-N-methylamino)-ethyl (±)-1,4-dihydro-5-isopropoxy-2-methyl-4-(3-nitrophenyl)-1,6-naphthyridine-3-carboxylate dihydrochloride (1.t); mp 148°–150° C., recrystallized from ethyl acetate/acetonitrile 2-dimethylaminoethyl (±)-1,4-dihydro-5-isopropoxy-2-methyl-4-(3-nitrophenyl)-1,6-naphthyridine-3-carboxylate dihydrochloride (1.u); mp 148°–150° C., recrystallized from diisopropyl ether 2-methylthio-ethyl (±)-1,4-dihydro-5-isopropoxy-2-methyl-4-(3-nitrophenyl)-1,6-naphthyridine-3-carboxylate (1.v); mp 154°–155° C., recrystallized from diisopropyl ether/ethyl acetate 2-(N-benzyl-N-methylamino)-ethyl (±)-1,4-dihydro-5-isopropoxy-2-methyl-4-(2-trifluoromethylphenyl)-1,6-naphthyridine-3-carboxylate dihydrochloride (1.w); mp 163°–165° C. (decomp.), recrystallized from acetonitrile diethyl (±)-1,4-dihydro-5-isopropoxy-2-methyl-4-(2-trifluoromethylphenyl)-1,6-naphthyridine-3,8-dicarboxylate (1.x); mp 140°–141° C., recrystallized from n-hexane ethyl (±)-1,4-dihydro-5-isopropoxy-2-methyl-4-(2-trifluoromethylphenyl)-1,6-naphthyridine-3-carboxylate hydrochloride (1.y); mp 137° C., recrystallized from ethyl acetate ethyl (±)-1,4-dihydro-5-isopropoxy-4-(2-methoxyphenyl)-2-methyl-1,6-naphthyridine-3-carboxylate (1.z); mp 145°–146° C., recrystallized from n-hexane/diisopropyl ether ethyl (±)-1,4-dihydro-5-isopropoxy-2-methyl-4-(2-thienyl)-1,6-naphthyridine-3-carboxylate (1.aa); mp 110°–111° C., recrystallized from n-hexane ethyl (±)-4-(2-cyanophenyl)-1,4-dihydro-5-isopropoxy-2-methyl-1,6-naphthyridine-3-carboxylate (1.ab); mp 182°–183° C., recrystallized from n-hexane/diisopropyl ether ethyl (±)-5-benzyloxy-1,4-dihydro-2-methyl-4-(2-trifluoromethylphenyl)-1,6-naphthyridine-3-carboxylate (1.ac); mp 142°–143° C., recrystallized from n-hexane/diisopropyl ether ethyl (±)-2-ethyl-1,4-dihydro-5-isopropoxy-8-methyl-4-(2-trifluoromethylphenyl)-1,6-naphthyridine-3-carboxylate (1.ad); mp 112°–113° C., recrystallized from n-hexane benzyl (±)-1,4-dihydro-5-isopropoxy-2-methyl-4-(2-trifluoromethylphenyl)-1,6-naphthyridine-3-carboxylate (1.ae); mp 126°–127° C., recrystallized from n-hexane 2-dimethylaminoethyl (±)-1,4-dihydro-5-isopropoxy-2-methyl-4-(2-trifluoromethylphenyl)-1,6-naphthyridine-3-carboxylate (1.af); mp 104°–105° C., recrystallized from n-hexane 3-dimethylaminopropyl (±)-1,4-dihydro-5-isopropoxy-2-methyl-4-(3-nitrophenyl)-1,6-naphthyridine-3-carboxylate (1.ag); mp 134°–136° C., recrystallized from n-hexane/diisopropyl ether ethyl (±)-4-(2-difluoromethoxyphenyl)-1,4-dihydro-5-isopropoxy-2-methyl-1,6-naphthyridine-3-carboxylate (1.ah); mp 145°–147° C., recrystallized from n-hexane/diisopropyl ether 2-dibenzylaminoethyl (±)-1,4-dihydro-5-isopropoxy-2-methyl-4-(2-trifluoromethylphenyl)-1,6-naphthyridine-3-carboxylate (1.ai); mp 131°–132° C., recrystallized as the sesquiphosphate from isopropanol ethyl (±)-1,4-dihydro-5-isopropoxy-2-methyl-4-(2-methylphenyl)-1,6-naphthyridine-3-carboxylate (1.aj); mp 122°–124° C., recrystallized from n-hexane/diisopropyl ether 2-dimethylaminoethyl (±)-1,4-dihydro-5-isopropoxy-2-methyl-4-(3-nitrophenyl)-1,6-naphthyridine-3-carboxylate (1.ak); mp 91°–93° C., recrystallized from n-hexane/diisopropyl ether (±)-1,4-dihydro-5-isopropoxy-2-methyl-4-(2-trifluoromethylphenyl)-1,6-naphthyridine-3-carboxylic acid-(2-aminoethyl) ester (1.al); mp 166°–167° C. from diisopropyl ether/ethyl acetate (±)-4-(2-difluoromethylthiophenyl)-1,4-dihydro-5-isopropoxy-2-methyl-1,6-naphthyridine-3-carboxylic acid ethyl ester (1.am); mp 124°–125° C. from n-hexane/diisopropyl ether (±)-1,4-dihydro-5-isopropoxy-2-methyl-4-(2,3-methylenedioxyphenyl)-1,6-naphthyridine-3-carboxylic acid ethyl ester (1.an); mp 156°–158° C. from diisopropyl ether/ethyl acetate (±)-1,4-dihydro-5-isopropoxy-2-methyl-4-(2-trifluoromethylphenyl)-1,6-naphthyridine-3-carboxylic acid-(2-piperidinoethyl) ester (1.ao); mp 118°–120° C. from n-hexane (±)-4-(2-chlorophenyl)-1,4-dihydro-5-isopropoxy-2-methyl-1,6-naphthyridine-3-carboxylic acid ethyl ester (1.ap); mp 135°–136° C. from n-hexane (±)-1,4-dihydro-5-isopropoxy-2-methyl-4-phenyl-1,6-naphthyridine-3-carboxylic acid ethyl ester (1.aq); mp 136°–137° C. from n-hexane (±)-1,4-dihydro-5-isopropoxy-2-methyl-4-(2-trifluoromethylphenyl)-1,6-naphthyridine-3-carboxylic acid-[3-(N-benzyl-N-methylamino)propyl]ester.dihydrochloride (1.ar); mp 143°–144° C. from dioxane/acetonitrile (4RS)-1,4-dihydro-5-isopropoxy-2-methyl-4-(2-trifluoromethylphenyl)-1,6-naphthyridine-3-carboxylic acid-(R)-2-butylester (1.as); mp 100° C. from n-hexane (4RS)-5-[(RS)-sec-butoxy]-1,4-dihydro-2-methyl-4-(2-trifluoromethylphenyl)-1,6-naphthyridine-3-carboxylic acid-[2-N-benzyl-N-methylamino)ethyl]ester.-dihydrochloride (1.at); mp 149°–152° C. from acetonitrile ethyl (±)-4-(2,1,3-benzoxadiazol-4-yl)-1,4-dihydro-5-isopropoxy-2-methyl-1,6-naphthyridine-3-carboxylate (1.au); mp 134°–136° C. from n-hexane N-benzyl-3-piperidinyl-(±)-1,4-dihydro-5-isopropoxy-2-methyl-4-(2-trifluoromethylphenyl)-1,6-naphthyridine-3-carboxylate (1.av); mp 205°–207° C. from diisopropyl ether/ethyl acetate N-benzyl-4-piperidinyl-(±)-1,4-dihydro-5-isopropoxy-2-methyl-4-(2trifluoromethylphenyl)-1,6-naphthyridine-3-carboxylate.sesquiphosphate (1.aw); mp 147°–148° C. from isopropanol

[2-(N,N-dibenzylamino)ethyl]-(±)-1,4-dihydro-5-isopropoxy-2-methyl-4-(2-trifluoromethylphenyl)-1,6-naphthyridine-3-carboxylate.sesquiphosphate (1.ax); mp 132°–133° C. from isopropanol

[2-(N-methyl-N-phenylamino)ethyl]-(±)-1,4-dihydro-5-isopropoxy-2-methyl-4-(2-trifluoromethylphenyl)-1,6-naphthyridine-3-carboxylate (1.ay); mp 114°–116° C. from n-hexane/diisopropyl ether ethyl (±)-4-(2-chloro-3-trifluoromethylphenyl)-1,4-dihydro-5-isopropoxy-2-methyl-1,6-naphthyridine-3-carboxylate (1.az); mp 173°–175° C. from n-hexane/diisopropyl ether

[2-(N,N-diethylamino)ethyl]-(±)-1,4-dihydro-5-isopropoxy-2-methyl-4-(2-trifluoromethylphenyl)-1,6-naphthyridine-3-carboxylate.hydrochloride (1.ba); mp 198°–200° C. from isopropanol ethyl (±)-1,4-dihydro-5-isopropoxy-2-methyl-4-(3-trifluoromethylphenyl)-1,6-naphthyridine-3-carboxylate (1.bb); mp 130°–131° C. from n-hexane ethyl (±)-1,4-dihydro-5-isopropoxy-2-methyl-4-(4-trifluoromethylphenyl)-1,6-naphthyridine-3-carboxylate (1.bc); mp 117°–120° C. from n-hexane ethyl (±)-1,4-dihydro-5-isopropoxy-2-methyl-4-(2-pyridyl)-1,6-naphthyridine-3-carboxylate (1.bd); mp 191°–193° C. from cyclohexane/ethyl acetate ethyl (±)-1,4-dihydro-5-ethoxy-2-methyl-4-(2-trifluoromethylphenyl)-1,6-naphthyridine-3-carboxylate (1.be); mp 91°–94° C. from n-hexane ethyl (±)-1,4-dihydro-2-methyl-5-propoxy-4-(2-trifluoromethylphenyl)-1,6-naphthyridine-3-carboxylate (1.bf); mp 115°–117° C. from n-hexane

[2-(N-benzyl-N-methylamino)ethyl]-(±)-4-(2-chloro-3-trifluoromethylphenyl)-1,4-dihydro-5-isopropoxy-2-methyl-1,6-naphthyridine-3-carboxylate.dihydrochloride (1.bg); mp>165° C. (decomp.) from isopropanol

[2-(N-benzyl-N-methylamino)ethyl]-(±)-1,4-dihydro-5-isobutoxy-2-methyl-4-(2-trifluoromethylphenyl)-1,6-naphthyridine-3-carboxylate.dihydrochloride (1.bh); mp 148°–150° C. from acetonitrile

[2-(N-benzyl-N-methylamino)ethyl]-(±)-4-(2-cyanophenyl)-1,4-dihydro-5-isopropoxy-2-methyl-1,6-naphthyridine-3-carboxylate (1.bi); mp 120°–122° C. from diisopropyl ether/ethyl acetate (2-phenoxyethyl)-(±)-1,4-dihydro-5-isopropoxy-2-methyl-4-(2-trifluoromethylphenyl)-1,6-naphthyridine-3-carboxylate.sesquioxalate (1.bj); mp 110°–113° C. from diisopropyl ether

[2-(N-benzyl-N-methylamino)ethyl]-(±)-1,4-dihydro-5-methoxy-2-methyl-4-(2-trifluoromethylphenyl)-1,6-naphthyridine-3-carboxylate.sesquioxalate (1.bk); mp 144°–146° C. (decomp.) from ethyl acetate/isopropanol methyl (±)-4-(2,6-dichlorophenyl)-1,4-dihydro-5-isopropoxy-2-methyl-1,6-naphthyridine-3-carboxylate (1.bl); mp 245° C. from diisopropyl ether/ethyl acetate (2-phenoxyethyl)-(±)-1,4-dihydro-5-isobutoxy-2-methyl-4-(2-trifluoromethylphenyl)-1,6-naphthyridine-3-carboxylate.hydrobromide (1.bm); mp 108°–109° C. from ether (2-phenoxyethyl)-4-(2-difluoromethoxyphenyl)-1,4-dihydro-5-isopropoxy-2-methyl-1,6-naphthyridine-3-carboxylate (1.bn); mp 122°–124° C. from diisopropyl ether benzyl (±)-1,4-dihydro-5-isopropoxy-2-methyl-4-(3-nitrophenyl)-1,6-naphthyridine-3-carboxylate (1.bo); mp 158°–160° C. from ethanol cyclopropylmethyl (±)-1,4-dihydro-5-isopropoxy-2-methyl-4-(2-trifluoromethylphenyl)-1,6-naphthyridine-3-carboxylate (1.bp); mp 112°–114° C. from n-hexane ethyl (±)-1,4-dihydro-5-isopropoxy-2-methyl-4-(3-nitrophenyl)-1,6-naphthyridine-3-carboxylate (1.bq); mp 180°–182° from n-hexane/ethyl acetate (trans-cinnamyl)-(±)-1,4-dihydro-5-isopropoxy-2-methyl-4-(2-trifluoromethylphenyl)-1,6-naphthyridine-3-carboxylate.sesquioxalate (1.br); mp 164°–166° C. from ethyl acetate

[2-(N-benzyl-N-methylamino)ethyl]-(±)-4-(2-chloro-3-trifluoromethylphenyl)-1,4-dihydro-5-isobutoxy-2-methyl-1,6-naphthyridine-3-carboxylate.dihydrochloride (1.bs); mp>140° C. (decomp.) from diisopropyl ether/acetonitrile (N-benzyl-3-pyrrolidinylmethyl)-(±)-1,4-dihydro-5-isopropoxy-2-methyl-4-(3-nitrophenyl)-1,6-naphthyridine-3-carboxylate (1.bt); mp 125°–128° C. from diisopropyl ether ethyl (±)-1,4-dihydro-5-isopropoxy-2-methyl-4-(2-trifluoromethylphenyl)-1,6-naphthyridine-3-carboxylate (1.bu); mp 130°–131° C. from n-hexane ethyl (−)-1,4-dihydro-5-isopropoxy-2-methyl-4-(2-trifluoromethylphenyl)-1,6-naphthyridine-3-carboxylate (1.bv); mp 130°–131° C. from n-hexane

[2-(N-benzyl-N-methylamino)ethyl]-(+)-1,4-dihydro-5-isopropoxy-2-methyl-4-(2-trifluoromethylphenyl)-1,6-naphthyridine-3-carboxylate.dihydrochloride (1.bw); mp>137° C. (decomp.) from ether

[2-(N-benzyl-N-methylamino)ethty]-(−)-1,4-dihydro-5-isopropoxy-2-methyl-4-(2-trifluoromethylphenyl)-1,6-naphthyridine-3-carboxylate.dihydrochloride (1.bx); mp>136° C. (decomp.) from ether (2-trimethylammonioethyl)-(±)-1,4-dihydro-5-isopropoxy-2-methyl-4-(3-nitrophenyl)-1,6-naphthyridine-3-carboxylate iodide (1.by); mp 149°–150° C. from ethanol

EXAMPLE 2

Methyl (±)-1,4-dihydro-5-methoxy-2-methyl-4-phenyl-1,6-naphthyridine-3-carboxylate Five g (17 mMol) methyl (±)-1,4,5,6-tetrahydro-2-methyl-5-oxo-4-phenyl-1,6-naphthyridine-3-carboxylate and 5 g (34 mMol) trimethyloxonium tetrafluoroborate in 200 ml 1,2-dichloroethane are stirred for 1.5 hours at ambient temperature under an atmosphere of nitrogen. The reaction mixture is shaken out with 50 ml water and the organic phase is separated off and evaporated on a rotary evaporator. After recrystallization of the residue from isopropanol, there is obtained the tetrafluoroborate of the desired compound. This is stirred with a saturated aqueous solution of potassium hydrogen carbonate and diethyl ether and the ethereal solution is separated off, dried over anhydrous sodium sulphate and evaporated on a rotary evaporator. Crystallization of the free base from 50 ml n-hexane/diisopropyl ether (2:1 v/v) gives colorless crystals; mp 210°–212° C.

The methyl (±)-1,4,5,6-tetrahydro-2-methyl-5-oxo-4-phenyl-1,6-naphthyridine-3-carboxylate used as starting material is prepared analogously to Example 1 with the use of methyl 1,4-dihydro-2,6-dimethyl-4-phenylpyridine-3,5-dicarboxylate.

The following compounds are obtained in an analogous manner:

ethyl (±)-4-(2-chlorophenyl)-1,4-dihydro-5-methoxy-2-methyl-1,6-naphthyridine-3-carboxylate (2.a); mp 173°–174° C., recrystallized from n-hexane/diisopropyl ether ethyl (±)-1,4-dihydro-5-methoxy-2-methyl-4-(3-nitrophenyl)-1,6-naphthyridine-3-carboxylate (2.b); mp 184°–186° C., recrystallized from diisopropyl ether/ethanol ethyl (±)-4-(2-fluorophenyl)-1,4-dihydro-5-methoxy-2-methyl-1,6-naphthyridine-3-carboxylate (2.c); mp .148°–150° C., recrystallized from n-hexane ethyl (±)-1,4-dihydro-5-methoxy-2-methyl-4-(2-trifluoromethylphenyl)-1,6-naphthyridine-3-carboxylate (2.d); mp 118°–120° C., recrystallized from n-hexane methyl (±)-4-(3-chloro-2-fluorophenyl)-1,4-dihydro-5-methoxy-2-methyl-1,6-naphthyridine-3-carboxylate (2.e); mp 214°–216° C., recrystallized from diisopropyl ether/methanol methyl (±)-4-(2-bromophenyl)-1,4-dihydro-5-methoxy-2-methyl-1,6-naphthyridine-3-carboxylate (2.f); mp 204°–205° C., recrystallized from diisopropyl ether/methanol (±)-1,4-dihydro-5-methoxy-2-methyl-4-(2-trifluoromethylphenyl)-1,6-naphthyridine-3-carboxylic acid(2-dimethylaminoethyl)ester (2.g); mp 137°–138° C. from ethyl acetate

EXAMPLE 3

(±)-1,4-Dihydro-5-isopropoxy-2-4-(2-trifluoromethylphenyl)-1,6-naphthyridine-3-carboxylic acid Three g (6.2 mMol) benzyl (±)-1,4-dihydro-5-isopropoxy-2-methyl-4-(2-trifluoromethylphenyl)-1,6-naphthyridine-3-carboxylate are hydrogenated at normal pressure and at ambient temperature with the use of 1.5 g 10% palladium on active charcoal in 100 ml ethanol. The take up of hydrogen is finished after 30 minutes. The catalyst is filtered off, the solvent is distilled off in a vacuum and the colorless, crystalline residue is recrystallized from diisopropyl ether/ethyl acetate. There is obtained (±)-1,4-dihydro-5-isopropoxy-2-methyl-4-(2-trifluoromethylphenyl)-1,6-naphthyridine-3-carboxylic acid in the form of colorless crystals with a melting point of 164°–166° C. (decomp.).

The benzyl (±)-1,4-dihydro-5-isopropoxy-2-methyl-4-(2-trifluoromethylphenyl)-1,6-naphthyridine-3-carboxylate used as starting material is prepared analogously to Example 1 with the use of dibenzyl 1,4-dihydro-2,6-dimethyl-4-(2-trifluoromethylphenyl)pyridine-3,5-dicarboxylate.

Obtained in an analogous manner is (±)-1,4-dihydro-5-methoxy-2-methyl-4-(2-trifluoromethylphenyl)-1,6-naphthyridine-3-carboxylic acid-(2-dimethylaminoethyl)-ester (3.a); mp 137°–138° C. from ethyl acetate.

EXAMPLE 4

Ethyl (±)-1,4-dihydro-5-isopropoxy-2-methyl-4-(2-trifluoromethylphenyl)-1,6-naphthyridine-3-carboxylate 1.3 g (43 mMol) sodium hydride (80% in paraffin oil) are suspended in 200 ml dry dimethylformamide and 12.5 g (33 mMol) ethyl (±)-1,4,5,6-tetrahydro-2-methyl-5-oxo-4-(2-trifluoromethylphenyl)-1,6-naphthyridine-3-carboxylate is added in portions thereto at ambient temperature, while stirring. After cessation of the evolution of gas, the reaction mixture is further stirred for 15 minutes at ambient temperature. 7.2 g (43 mMol) isopropyl iodide is then added. Stirring is continued for three days at ambient temperature. The solvent is evaporated off in vacuo and after adding of 500 ml water the residue is treated in the ultrasonic bath for 30 minutes. The resulting crystalline mass is filtered off and dried at 50° C.

For purification of the crude product, it is dissolved in ethyl acetate and chromatographed over silica gel with toluene/ethyl acetate (3:1 v/v). The solvent of the fractions of Rf 0,4 is evaporated in vacuo and the residue is stirred till crystallization with n-hexane. The product is filtered off and recrystallized from 60 ml n-hexane. Colorless crystals are obtained, mp 102°–103° C.

The ethyl (±)-1,4,5,6-tetrahydro-2-methyl-5-oxo-4-(2-trifluoromethylphenyl)-1,6-naphthyridine-3-carboxylate used as starting material is prepared as follows:

A solution of 79.2 g (0.2 mol) diethyl 1,4-dihydro-2,6-dimethyl-4-(2-trifluoromethylphenyl)pyridin-3,5-dicarboxylate in 400 ml dimethylformamide is added dropwise, under an atmosphere of nitrogen, to a suspension of 6.0 g (0.2 mol) sodium hydride (80% in paraffin oil) in 100 ml dry dimethylformamide. Upon slowing down of the evolution of gas, the reaction mixture is further stirred for ten minutes at ambient temperature and subsequently 16.2 g (0.2 mol) s-triazine in 300 ml dimethylformamide are added dropwise thereto. The reaction mixture is heated to 110° C. for 16 hours under stirring and, after cooling, evaporated in a vacuum. The residue is stirred with 1.5 l acetone, filtered and the filtrate evaporated in a vacuum. The residue is chromatographed over silica gel with dichloromethane/methanol (9:1 v/v). The fraction with Rf 0.45 is stirred with 200 ml chloroform the pale beige crystals are filtered off. For further purification they are recrystallized from ethanol and colorless crystals are obtained, mp 261° C.

The diethyl 1,4-dihydro-2,6-dimethyl-4-(2-trifluoromethylphenyl)pyridin-3,5-dicarboxylate used as starting material is prepared as follows:

Fifty g (0.29 mol) 2-trifluoromethyl benzaldehyde and 76 g (0.58 mol) ethyl acetoacetate in 30 ml aqueous ammonia are boiled for 16 hours with 200 ml ethanol. The product, precipitated after cooling, is filtered off and washed with cold ethanol. Pale beige crystals are obtained, mp 142°–143° C.

The following comparative experiments demonstrate the pharmacologically effectiveness of the compounds of general formula (I)':

(a) Isolated smooth muscle

Isolated smooth muscle from rabbits (blood vessel rings, A. basilaris, A. coronaria, A. saphena) are fixed in an organ bath in such a manner that isometric contractions can be measured. The contraction is initiated by a potassium depolarization in tyrode solution. The experimental protocol is a known standard model for the recognition of compounds which block the calcium canals opened in the potassium depolarization (Fleckenstein, 1983). As can be seen from the following Table 1, some substances act semi-maximally relaxingly in the nanomolar range. In part, this potency considerably exceeded that of the already known calcium antagonists diltiazem and nifedipine.

(b) Isolated papillary muscle

Papillary muscle from the left ventricle of the guinea pig is fixed, as in the case of isolated vessels, in an organ bath for isometric contraction measurement and electrically stimulated by field stimulation with a frequency of 250/min (stimulation period 10 msec, amplitude supramaximal). The following Table 2 shows that the compounds display their calcium antagonist action selectively on the smooth vessel muscle and on the myocardium show surprisingly, in the therapeutic range (1–100 nmolar) no negative but in part even positive inotropic action. However, it cannot be excluded that the dimethyl sulfoxide used as a solvent has contributed to the observed positive inotropic action. The compound of Example 1(c) possess, at a therapeutic concentration of $3 \times 10^{-7}$ mol/liter, a maximum increase of the contractility of 36% and at a concentration of $4 \times 10^{-9}$ mol/liter, this is +18%.

TABLE 1

Table 1 shows concentrations ($IC_{50}$, mol/l) of compounds (I) which bring about a semi-maximum inhibition of the K+ depolarization contraction of blood vessel rings in an organ bath. For comparison, there is given the $IC_{50}$ values of the calcium antagonists diltiazem and nifedipine.

| Compound of Example No. | A. bas.[1] | A. cor.[2] | A. saph.[3] |
|---|---|---|---|
| 1 | $5 \times 10^{-9}$ | $3 \times 10^{-8}$ | $7 \times 10^{-9}$ |
| 1a | $2.4 \times 10^{-9}$ | $2.7 \times 10^{-9}$ | $8 \times 10^{-9}$ |
| 1h | $3 \times 10^{-6}$ | $1.5 \times 10^{-8}$ | $1 \times 10^{-6}$ |
| 1b | $6.6 \times 10^{-10}$ | $7.5 \times 11^{-10}$ | $3.4 \times 10^{-9}$ |
| 1c | $1.5 \times 10^{-8}$ | $6.5 \times 10^{-8}$ | $1 \times 10^{-6}$ |
| 1g | $5.9 \times 10^{-9}$ | $3.2 \times 10^{-9}$ | — |
| 1l | $7.4 \times 10^{-9}$ | $3.1 \times 10^{-8}$ | $3.9 \times 10^{-7}$ |
| 1p | $1.6 \times 10^{-8}$ | $5.3 \times 10^{-8}$ | — |
| 1q | $3.5 \times 10^{-8}$ | $1.9 \times 10^{-7}$ | — |
| 2 | $2.5 \times 10^{-7}$ | $1 \times 10^{-6}$ | $9 \times 10^{-8}$ |
| 2a | $6 \times 10^{-9}$ | $1 \times 10^{-8}$ | $6 \times 10^{-7}$ |
| 2b | $1.8 \times 10^{-9}$ | $1.2 \times 10^{-8}$ | $6 \times 10^{-7}$ |
| diltiazem | $1.2 \times 10^{-7}$ | $1.7 \times 10^{-7}$ | $2.9 \times 10^{-6}$ |
| nifedipine | $2.7 \times 10^{-9}$ | $5 \times 10^{-9}$ | $5.9 \times 10^{-8}$ |

[1] A. bas. = arteria basilaris
[2] A. cor. = arteria coronaria
[3] A. saph. = arteria saphena
obtained from rabbits; average diameter 0.5–1.0 mm

TABLE 2

Changes of the contraction amplitude of isolated papillary muscle of the guinea pig (stimulation frequency 250/min, stimulation time 10 msec, stimulation amplitude 10–20 V field stimulation). IC = inhibition concentration, $IC_{100}$ corresponds to maximum action. $\Delta\%$ = maximum decrease of the contractility. The inhibiting concentrations of diltiazem and nifedipine are given for comparison.

| Compound of Example No. | Number of Animals | $IC_{50}/100$ | $\Delta\%$ |
|---|---|---|---|
| 1 | (n = 7) | $3.10^{-4}$ | −40 |
| 1a | (n = 4) | $3.10^{-4}$ | −48 |
| 1h |  | $1.10^{-4}$ | −38 |
| 1l |  | $1.2.10^{-4}$ | −38 |
| 1p |  | $1.10^{-5}$ | −23 |
| 1q |  | $1.10^{-5}$ | −7 |
| 1h | (n = 4) | $3.10^{-4}$ | −54 |
| diltiazem | (n = 6) | $10^{-5}$ | −60 |
| nifedipine* |  | $10^{-6}$ | −80 |

*Hof and Scholtysik, J. Cardiovasc. Pharmacol. 5:176-183, 1983), Experiments on the papillary muscle of the rabbit.

Table 2 shows the maximum actions on the contractility in the case of the concentration necessary herefor ($IC_{100}$=inhibitory concentration). From this, it can be seen that the comparison compounds, even in the case of considerably lower concentrations ($IC_{100}$), show a higher decrease of the contractility. The concentration $IC_{100}$ lies far outside of the therapeutic range of the compounds according to the present invention so that a negative inotropism is there not to be found. It follows from this that the therapeutic safety of the compounds according to the present invention is considerably increased in comparison with the prior art.

We claim:

1. A compound selected from the group consisting of:
   ethyl (±)-4-(2-chloro-3-trifluoromethylphenyl)-1,4-dihydro-5-isopropoxy-2-methyl-1,6-naphthyridine-3-carboxylate,

[2-(N,N-diethylamino)ethyl]-(±)-1,4-dihydro-5-isopropoxy-2-methyl-4-(2-trifluoromethylphenyl)-1,6-naphthyridine-3-carboxylate, ethyl (±)-1,4-dihydro-5-isopropoxy-2-methyl-4-(3-trifluoromethylphenyl)-1,6-naphthyridine-3-carboxylate, ethyl (±)-1,4-dihydro-5-isopropoxy-2-methyl-4-(4-trifluoromethylphenyl)-1,6-naphthyridine-3-carboxylate, ethyl (±)-1,4-dihydro-5-isopropoxy-2-methyl-4-(2-pyridyl)-1,6-naphthyridine-3-carboxylate, ethyl (±)-1,4-dihydro-5-ethoxy-2-methyl-4-(2-trifluoromethylphenyl)-1,6-naphthyridine-3-carboxylate, ethyl (±)-1,4-dihydro-2-methyl-5-propoxy-4-(2-trifluoromethylphenyl)-1,6-naphthyridine-3-carboxylate,

[2-(N-benzyl-N-methylamino)ethyl]-(±)-4-(2-chloro-3-trifluoromethylphenyl)-1,4-dihydro-5-isopropoxy-2-methyl-1,6-naphthyridine-3-carboxylate,

[2-(N-benzyl-N-methylamino)ethyl]-(±)-1,4-dihydro-5-isobutoxy-2-methyl-4-(2-trifluoromethylphenyl)-1,6-naphthyridine-3-carboxylate,

[2-(N-benzyl-N-methylamino)ethyl]-(±)-4-(2-cyanophenyl)-1,4-dihydro-5-isopropoxy-2-methyl-1,6-naphthyridine-3-carboxylate, (2-phenoxyethyl)-(±)-1,4-dihydro-5-isopropoxy-2-methyl-4-(2-trifluoromethylphenyl)-1,6-naphthyridine-3-carboxylate,

[2-(N-benzyl-N-methylamino)ethyl]-(±)-1,4-dihydro-5-methoxy-2-methyl-4-(2-trifluoromethylphenyl)-1,6-naphthyridine-3-carboxylate, methyl (±)-4-(2,6-dichlorophenyl)-1,4-dihydro-5-isopropoxy-2-methyl-1,6-naphthyridine-3-carboxylate, (2-phenoxyethyl)-(±)-1,4-dihydro-5-isobutoxy-2-methyl-4-(2-trifluoromethylphenyl)-1,6-naphthyridine-3-carboxylate, (2-phenoxyethyl)-4-(2-difluoromethoxyphenyl)-1,4-dihydro-5-isopropoxy-2-methyl-1,6-naphthyridine-3-carboxylate, benzyl (±)-1,4-dihydro-5-isopropoxy-2-methyl-4-(3-nitrophenyl)-1,6-naphthyridine-3-carboxylate, cyclopropylmethyl (±)-1,4-dihydro-5-isopropoxy-2-methyl-4-(2-trifluoromethylphenyl)-1,6-naphthyridine-3-carboxylate, ethyl (±)-1,4-dihydro-5-isopropoxy-2-methyl-4-(3-nitrophenyl)-1,6-naphthyridine-3-carboxylate, (trans-cinnamyl)-(±)-1,4-dihydro-5-isopropoxy-2-methyl-4-(2-trifluoromethylphenyl)-1,6-naphthyridine-3-carboxylate,

[2-(N-benzyl-N-methylamino)ethyl]-(±)-4-(2-chloro-3-trifluoromethylphenyl)-1,4-dihydro-5-isobutoxy-2-methyl-1,6-naphthyridine-3-carboxylate, (N-benzyl-3-pyrrolidinylmethyl)-(±)-1,4-dihydro-5-isopropoxy-2-methyl-4-(3-nitrophenyl)-1,6-naphthyridine-3-carboxylate, ethyl (−)-1,4-dihydro-5-isopropoxy-2-methyl-4-(2-trifluoromethylphenyl-1,6-naphthyridine-3-carboxylate,

[2-(N-benzyl-N-methylamino)ethyl]-(±)-1,4-dihydro-5-isopropoxy-2-methyl-4-(2-trifluoromethylphenyl)-1,6-naphthyridine-3-carboxylate,

[2-N-benzyl-N-methylamino)ethyl]-(−)-1,4-dihydro-5-isopropoxy-2-methyl-4-(2-trifluoromethylphenyl)-1,6-naphthyridine-3-carboxylate, and (2-trimethylammonioethyl)-(±)-1,4-dihydro-5-isopropoxy-2-methyl-4-(3-nitrophenyl)-1,6-naphthyridine-3-carboxylate iodide, or a pharmacologically acceptable salt thereof.

2. A pharmaceutical composition for treating blood vessel diseases comprising an effective amount of a compound according to claim 1 in admixture with a solid or liquid pharmaceutical diluent or carrier.

3. A method for treating diseases of blood vessels which comprises treating a host suffering therefrom with a pharmaceutical composition according to claim 2 in unit dosage form.

* * * * *